United States Patent
Carpentier

(10) Patent No.: US 11,253,729 B2
(45) Date of Patent: Feb. 22, 2022

(54) EXTERNAL ULTRASOUND GENERATING TREATING DEVICE FOR SPINAL CORD AND/OR SPINAL NERVE TREATMENT, APPARATUS COMPRISING SUCH DEVICE AND METHOD

(71) Applicants: SORBONNE UNIVERSITE, Paris (FR); ASSISTANCE PUBLIQUE—HÔPITAUX DE PARIS, Paris (FR)

(72) Inventor: Alexandre Carpentier, Paris (FR)

(73) Assignees: SORBONNE UNIVERSITE, Paris (FR); ASSISTANCE PUBLIQUE—HÔPITAUX DE PARIS, Paris (FR)

(*) Notice: Subject to any disclaimer, the term of this patent is extended or adjusted under 35 U.S.C. 154(b) by 270 days.

(21) Appl. No.: 16/082,548

(22) PCT Filed: Mar. 11, 2016

(86) PCT No.: PCT/IB2016/000431
§ 371 (c)(1),
(2) Date: Sep. 6, 2018

(87) PCT Pub. No.: WO2017/153799
PCT Pub. Date: Sep. 14, 2017

(65) Prior Publication Data
US 2019/0038922 A1 Feb. 7, 2019

(51) Int. Cl.
*A61N 7/00* (2006.01)
*A61B 8/00* (2006.01)
*A61B 8/08* (2006.01)

(52) U.S. Cl.
CPC .............. *A61N 7/00* (2013.01); *A61B 8/0875* (2013.01); *A61B 8/4477* (2013.01); *A61B 8/481* (2013.01);

(Continued)

(58) Field of Classification Search
CPC ..... A61B 8/0875; A61B 8/4477; A61B 8/481; A61N 2007/0026; A61N 2007/0078; A61N 2007/0091; A61N 7/00
See application file for complete search history.

(56) References Cited

U.S. PATENT DOCUMENTS 1,879,502 A 9/1932 Rinman
4,646,756 A 3/1987 Watmough et al.
(Continued)

FOREIGN PATENT DOCUMENTS

CN 101152646 4/2008
CN 103142287 6/2013
(Continued)

*Primary Examiner* — Joanne M Bui Pho
*Assistant Examiner* — Alexei Bykhovski
(74) *Attorney, Agent, or Firm* — Clark & Brody LP

(57) ABSTRACT

An external ultrasound generating treating device (12) to induce spinal cord and/or spinal nerve treatment comprises at least two sub-arrays of ultrasound generating treatment transducers, a left sub-array (20iL) being located on a left lateral side and a right sub-array (20iR) being located on a right lateral side of the central longitudinal axis (Ai). The device comprises a support structure (32) having at least one module (34i) comprising a left lateral section (34iL) and a right lateral section (34iR). The support structure (32) maintains, in use of the device, a constant distance and a constant relative angular orientation around the central longitudinal axis (Ai) between the first left and first right treatment transducers or set of treatment transducers (20iL, 20iR). Also disclosed is an apparatus including the external ultrasound generating treating device (12) and methods of its use.

19 Claims, 2 Drawing Sheets

(52) U.S. Cl.
CPC .............. *A61N 2007/0026* (2013.01); *A61N 2007/0078* (2013.01); *A61N 2007/0091* (2013.01)

(56) References Cited

U.S. PATENT DOCUMENTS

| | | |
|---|---|---|
| 4,836,191 A | 6/1989 | Noske et al. |
| 5,321,104 A | 6/1994 | Sumino et al. |
| 5,501,655 A | 3/1996 | Rolt et al. |
| 5,524,624 A | 6/1996 | Tepper et al. |
| 5,752,515 A | 5/1998 | Jolesz et al. |
| 5,964,936 A | 10/1999 | Reisser |
| 6,139,241 A | 10/2000 | Craig et al. |
| 6,254,553 B1 | 7/2001 | Lidgren et al. |
| 6,254,624 B1 | 7/2001 | Oddsen et al. |
| 6,319,241 B1 | 11/2001 | King et al. |
| 6,468,219 B1 | 10/2002 | Njemanze |
| 6,560,486 B1 | 5/2003 | Osorio et al. |
| 6,613,005 B1 | 9/2003 | Friedman et al. |
| 6,666,833 B1 | 12/2003 | Friedman et al. |
| 6,862,479 B1 | 3/2005 | Whitehurst et al. |
| 7,101,337 B2 | 9/2006 | Aubry et al. |
| 7,107,104 B2 | 9/2006 | Keravel et al. |
| 7,211,060 B1 | 5/2007 | Talish et al. |
| 7,522,962 B1 | 4/2009 | Doron et al. |
| 7,575,550 B1 | 8/2009 | Govari |
| 7,878,977 B2 | 2/2011 | Mo et al. |
| 7,896,821 B1 | 3/2011 | Magnin et al. |
| 8,942,781 B2 | 1/2015 | Carpentier et al. |
| 8,977,361 B2 | 3/2015 | Carpentier et al. |
| 9,993,337 B1 | 6/2018 | Brogan et al. |
| 10,076,652 B2 | 9/2018 | Liu et al. |
| 10,512,445 B2 * | 12/2019 | Chen .................... A61B 8/4254 |
| 2001/0051819 A1 | 12/2001 | Fischell et al. |
| 2002/0002371 A1 | 1/2002 | Acker et al. |
| 2002/0038086 A1 | 3/2002 | Hynynen et al. |
| 2002/0072741 A1 | 6/2002 | Sliwa et al. |
| 2002/0177792 A1 | 11/2002 | Ooba et al. |
| 2003/0092987 A1 | 5/2003 | Hynynen et al. |
| 2003/0135135 A1 | 7/2003 | Miwa et al. |
| 2003/0195584 A1 | 10/2003 | Dawson |
| 2003/0225331 A1 | 12/2003 | Diederich et al. |
| 2004/0049134 A1 | 3/2004 | Tosaya et al. |
| 2004/0054282 A1 | 3/2004 | Aubry et al. |
| 2004/0116772 A1 | 6/2004 | Lupin et al. |
| 2004/0122323 A1 | 6/2004 | Vortman et al. |
| 2004/0162507 A1 | 8/2004 | Govari |
| 2005/0020945 A1 | 1/2005 | Tosaya et al. |
| 2005/0021117 A1 | 1/2005 | He et al. |
| 2005/0240170 A1 | 10/2005 | Zhang et al. |
| 2005/0283203 A1 | 12/2005 | Flaherty et al. |
| 2006/0049957 A1 | 3/2006 | Surgenor et al. |
| 2006/0079816 A1 | 4/2006 | Barthe et al. |
| 2006/0129204 A1 | 6/2006 | Pless et al. |
| 2006/0224060 A1 | 10/2006 | Garell et al. |
| 2006/0241529 A1 | 10/2006 | Hynynen et al. |
| 2007/0016041 A1 | 1/2007 | Nita |
| 2007/0038100 A1 | 2/2007 | Nita |
| 2007/0067003 A1 | 3/2007 | Sanchez et al. |
| 2007/0073135 A1 | 3/2007 | Lee et al. |
| 2007/0179558 A1 | 8/2007 | Gliner et al. |
| 2007/0219547 A1 | 9/2007 | Osypka |
| 2007/0225773 A1 | 9/2007 | Shen et al. |
| 2007/0293908 A1 | 12/2007 | Cowan et al. |
| 2008/0004676 A1 | 1/2008 | Osypka et al. |
| 2008/0140149 A1 | 6/2008 | John et al. |
| 2008/0183166 A1 | 7/2008 | Miller |
| 2008/0195160 A1 | 8/2008 | Wingeier et al. |
| 2008/0221490 A1 | 9/2008 | Zahos |
| 2008/0249409 A1 | 10/2008 | Fraser et al. |
| 2008/0275526 A1 | 11/2008 | Lozano |
| 2008/0287837 A1 | 11/2008 | Makin et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0082860 A1 | 3/2009 | Schieber et al. |
| 2009/0093724 A1 | 4/2009 | Pernot et al. |
| 2009/0112278 A1 | 4/2009 | Wingeier et al. |
| 2009/0112280 A1 | 4/2009 | Wingeier et al. |
| 2009/0149781 A1 | 6/2009 | Liu et al. |
| 2009/0238763 A1 | 9/2009 | Yu et al. |
| 2009/0248165 A1 | 10/2009 | Lin et al. |
| 2009/0254134 A1 | 10/2009 | Nikolov et al. |
| 2010/0010394 A1 | 1/2010 | Liu et al. |
| 2010/0041988 A1 | 2/2010 | Pijnenburg et al. |
| 2010/0056924 A1 | 3/2010 | Powers |
| 2010/0137937 A1 | 6/2010 | John et al. |
| 2010/0143241 A1 | 6/2010 | Johnson et al. |
| 2010/0145414 A1 | 6/2010 | Decre et al. |
| 2010/0160779 A1 | 6/2010 | Browning et al. |
| 2010/0217160 A1 | 8/2010 | Saguchi et al. |
| 2010/0222715 A1 | 9/2010 | Nita |
| 2010/0224950 A1 | 9/2010 | Dinyari et al. |
| 2010/0249597 A1 | 9/2010 | Shi |
| 2010/0268088 A1 | 10/2010 | Prus et al. |
| 2011/0040172 A1 | 2/2011 | Carpentier et al. |
| 2011/0046694 A1 | 2/2011 | Forsell |
| 2011/0051554 A1 | 3/2011 | Varray et al. |
| 2011/0089160 A1 | 4/2011 | Kuriki |
| 2011/0112394 A1 | 5/2011 | Mishelevich |
| 2011/0178441 A1 | 7/2011 | Tyler |
| 2011/0178442 A1 | 7/2011 | Mishelevich |
| 2011/0208095 A1 | 8/2011 | Jolesz et al. |
| 2011/0213200 A1 | 9/2011 | Mishelevich |
| 2011/0245734 A1 | 10/2011 | Wagner et al. |
| 2011/0295105 A1 | 12/2011 | Konofagou et al. |
| 2012/0010711 A1 | 1/2012 | Antonyshyn et al. |
| 2012/0046531 A1 | 2/2012 | Hua |
| 2012/0065458 A1 | 3/2012 | Tol |
| 2012/0078140 A1 | 3/2012 | Nita |
| 2012/0083719 A1 | 4/2012 | Mishelevich |
| 2012/0109019 A1 | 5/2012 | Schneider et al. |
| 2012/0123270 A1 | 5/2012 | Klee et al. |
| 2012/0130288 A1 * | 5/2012 | Holland .................... A61N 7/00 601/2 |
| 2012/0143058 A1 | 6/2012 | Powers et al. |
| 2012/0172949 A1 | 7/2012 | Wagenaar Cacciola et al. |
| 2012/0203079 A1 | 8/2012 | McLaughlin |
| 2012/0277639 A1 | 11/2012 | Pollock et al. |
| 2012/0283502 A1 | 11/2012 | Mishelevich et al. |
| 2012/0323147 A1 | 12/2012 | Scheirer et al. |
| 2013/0006106 A1 | 1/2013 | O'Reilly et al. |
| 2013/0046229 A1 | 2/2013 | Konofagou et al. |
| 2013/0049534 A1 | 2/2013 | Clark et al. |
| 2013/0079682 A1 | 3/2013 | Mishelevich |
| 2013/0131754 A1 | 5/2013 | Sarvazyan |
| 2013/0178764 A1 | 7/2013 | Eckhouse et al. |
| 2013/0178765 A1 | 7/2013 | Mishelevich |
| 2013/0204316 A1 | 8/2013 | Carpentier et al. |
| 2013/0251633 A1 | 9/2013 | Borden et al. |
| 2013/0281890 A1 | 10/2013 | Mishelevich |
| 2013/0324891 A1 | 12/2013 | Towe |
| 2013/0324892 A1 | 12/2013 | Zhu et al. |
| 2013/0331685 A1 | 12/2013 | Liu et al. |
| 2013/0338526 A1 | 12/2013 | Howard |
| 2014/0005521 A1 | 1/2014 | Kohler et al. |
| 2014/0074076 A1 * | 3/2014 | Gertner .................... A61B 6/12 606/12 |
| 2014/0114216 A1 | 4/2014 | Konofagou et al. |
| 2014/0249454 A1 | 9/2014 | Carpentier |
| 2014/0296646 A1 | 10/2014 | Wingeier et al. |
| 2014/0330123 A1 | 11/2014 | Manwaring et al. |
| 2015/0005614 A1 * | 1/2015 | Heggeness ................ A61F 7/00 600/407 |
| 2015/0005860 A1 | 1/2015 | Howard et al. |
| 2015/0045724 A1 | 2/2015 | Chen et al. |
| 2015/0065871 A1 | 3/2015 | Konofagou et al. |
| 2015/0133785 A1 | 5/2015 | Schlenger |
| 2015/0148710 A1 | 5/2015 | Towe et al. |
| 2015/0224345 A1 | 8/2015 | Warlick |
| 2015/0231417 A1 | 8/2015 | Metcalf et al. |
| 2015/0265305 A1 | 9/2015 | Stulen et al. |
| 2015/0297176 A1 | 10/2015 | Rincker et al. |
| 2016/0000411 A1 | 1/2016 | Raju et al. |

(56) References Cited

U.S. PATENT DOCUMENTS

| | | |
|---|---|---|
| 2016/0001096 A1 | 1/2016 | Mishelevich |
| 2016/0016012 A1 | 1/2016 | Youn et al. |
| 2016/0107002 A1 | 4/2016 | Nita |
| 2016/0151618 A1* | 6/2016 | Powers ................ A61B 8/4209 600/439 |
| 2016/0184614 A1* | 6/2016 | Matula ................... A61B 8/085 600/439 |
| 2016/0242648 A1 | 8/2016 | Konofagou et al. |
| 2018/0263602 A1 | 9/2018 | Elvira Seguro et al. |
| 2018/0353777 A1 | 12/2018 | Dianis et al. |
| 2021/0106849 A1 | 4/2021 | Liu et al. |

FOREIGN PATENT DOCUMENTS

| | | |
|---|---|---|
| DE | 31 50 513 | 6/1983 |
| DE | 19 641 935 | 9/1997 |
| DE | 10 2010 001020 | 7/2011 |
| EP | 0 111 386 | 6/1984 |
| EP | 0 643 982 | 3/1995 |
| EP | 0 701 840 | 3/1996 |
| EP | 0 872 262 | 10/1998 |
| EP | 1 262 160 | 12/2002 |
| EP | 1 312 423 | 5/2003 |
| EP | 1 774 989 | 4/2007 |
| EP | 1 806 238 | 7/2007 |
| EP | 1 834 646 | 9/2007 |
| GB | 2 445 585 | 7/2008 |
| GB | 2 473 265 | 3/2011 |
| GR | 20070100349 | 1/2009 |
| JP | 60-75809 | 4/1985 |
| JP | 05-68684 | 3/1993 |
| JP | 2001-327495 | 11/2001 |
| JP | 2003-325616 | 11/2003 |
| JP | 2007-289715 | 11/2007 |
| WO | 92/12605 | 7/1992 |
| WO | 92/22350 | 12/1992 |
| WO | 96/39079 | 12/1996 |
| WO | 98/47569 | 10/1998 |
| WO | 99/34758 | 7/1999 |
| WO | 00/78232 | 12/2000 |
| WO | 01/09111 | 2/2001 |
| WO | 02/43805 | 6/2002 |
| WO | 02/100480 | 12/2002 |
| WO | 03/059437 | 7/2003 |
| WO | 03/061756 | 7/2003 |
| WO | 2004/050175 | 6/2004 |
| WO | 2004/093725 | 11/2004 |
| WO | 2004/105640 | 12/2004 |
| WO | 2005/009244 | 2/2005 |
| WO | 2005/065738 | 7/2005 |
| WO | 2006/092061 | 9/2006 |
| WO | 2006/105463 | 10/2006 |
| WO | 2006/130445 | 12/2006 |
| WO | 2006/138702 | 12/2006 |
| WO | 2007/026299 | 3/2007 |
| WO | 2007/064453 | 6/2007 |
| WO | 2007/121133 | 10/2007 |
| WO | 2007/124458 | 11/2007 |
| WO | 2008/072125 | 6/2008 |
| WO | 2009/029141 | 3/2009 |
| WO | 2009/067323 | 5/2009 |
| WO | 2009/111317 | 9/2009 |
| WO | 2009/115523 | 9/2009 |
| WO | 2009/132855 | 11/2009 |
| WO | 2010/009141 | 1/2010 |
| WO | 2011/029208 | 3/2011 |
| WO | 2011/079177 | 6/2011 |
| WO | 2011/101492 | 8/2011 |
| WO | 2011/103098 | 8/2011 |
| WO | 2012/030522 | 3/2012 |
| WO | 2012/125172 | 9/2012 |
| WO | 2013/048912 | 4/2013 |
| WO | 2013/177430 | 11/2013 |
| WO | 2014/013285 | 1/2014 |
| WO | 2014/060914 | 4/2014 |
| WO | 2014/207665 | 12/2014 |
| WO | 2015/047103 | 4/2015 |
| WO | 2015/075603 | 5/2015 |
| WO | 2015/079324 | 6/2015 |

* cited by examiner

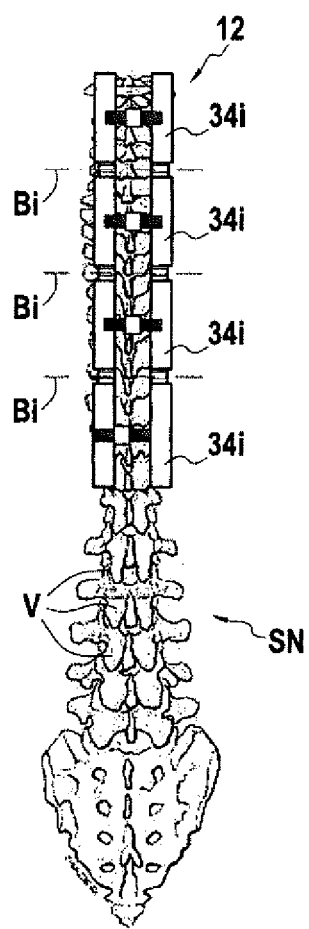
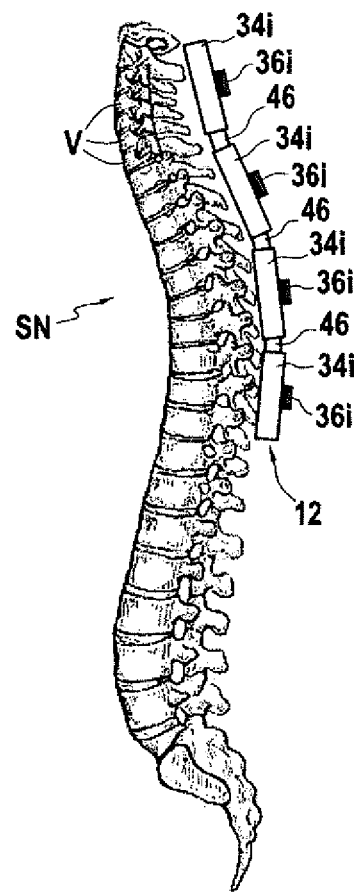
FIG.3  FIG.4
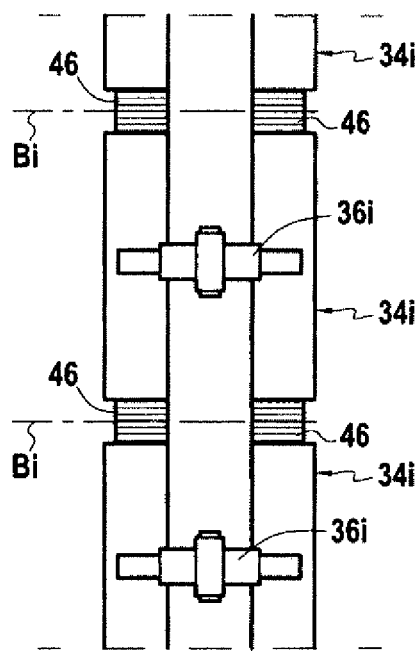
FIG.5

EXTERNAL ULTRASOUND GENERATING TREATING DEVICE FOR SPINAL CORD AND/OR SPINAL NERVE TREATMENT, APPARATUS COMPRISING SUCH DEVICE AND METHOD

TECHNICAL FIELD

The present invention relates to a device, an apparatus and a method for the treatment of spinal cord and/or spinal nerve disorders, especially for the transient disruption of the blood-spinal cord barrier and/or blood-spinal nerves barrier of a human.

BACKGROUND ART

The spinal cord and/or the spinal nerve(s) may to subject to various physiological disorders which induce different forms of pathologies. There is a clear need for improving therapies in this domain. Also, there is a need to improve the repair and/or rehabilitation treatments of the spinal cord and/or spinal nerve(s), for example for hemiplegia and paraplegia, including with cell transplant and/or stem cell regeneration.

Some available treatments include action of drugs on the spinal cord and/or spinal nerve tissues. However, the blood-spinal cord barrier (hereinafter BSCB) limits or prevents the penetration of therapeutic drugs in the spinal cord or nerve tissues. Similarly, the blood-spinal nerve barrier (hereinafter BSNB) prevents the penetration of therapeutic drugs in the spinal cord or nerve tissues.

It is known to use spinal drug delivery catheters inserted in the spinal canal, but this only allows injection of a fluid which only penetrates to a limited and insufficient extent into spinal cord or spinal nerve tissues.

Some documents suggest the use of spinal cord electrical stimulation, sometimes in association with drug delivery. U.S. Pat. No. 6,319,241 describes techniques for positioning therapy delivery elements within a spinal cord or a brain to provide electrical stimulation and/or drug infusion to a precise target. U.S. Pat. No. 6,862,479 describes implantable system control units (SCU) to apply one or more stimulating drugs and/or electrical pulses to a spinal section responsible for innervating the male reproductive organs. Such methods do not cause any significant opening of the blood spinal cord barrier.

WO-96/39079 describes a method and an apparatus for performing ultrasonic imaging of a region of a patient while simultaneously applying therapeutic ultrasonic waves to the region for rupturing vesicles administered to that region, for purposes such as enhanced cavitation or the targeted release of a bioactive agent contained in the vesicles into the region.

Many systems and methods have been disclosed which rely on high energy ultrasounds for causing an intended damage to the targeted tissue. US-2005/0240170 describes methods and systems for producing hemostasis, tissue closure, or vessel closure by inserting a thermal delivery probe into a passageway and emitting thermal energy from the probe to produce the hemostasis or tissue closure. The thermal delivery probe may have one or more ultrasound transducers positioned in an elongated shaft. GR20070100349 discloses an ultrasound diathermy system that can be applied to the spinal cord. It causes a cut and hemostasis in the tissues, it seals vessels of relatively small transection without causing their rupture.

US-2008/0287837 discloses an interstitial end effector which is interstitially insertable into patient tissue, which includes at least one medical-treatment ultrasound transducer, and which includes at least one end-effector-tissue-track ablation device. US-2007/073135, describes an integrated ultrasound imaging and ablation probe. EP-1774989 discloses an ultrasound probe which comprises one or more transducers positionable on, in proximity to or within a cancerous mass of tissue. The one or more transducers are capable of delivering sufficient levels of acoustic energy to (a) induce coagulative necrosis of a region of the tissue surrounding the transducer, and (b) induce sonoporation of a chemotherapy agent into cancer cells in the tumor and in the margins of tissue adjacent the necrosis region of tissue. EP-0643982 describes an ultrasound thermotherapy probe and method for treatment of prostate tissues. WO-2007/124458 describes a method of thermal treatment for myolysis and destruction of benign uterine tumors. JP-2007-289715 describes an ultrasonic diagnostic and therapeutic system in which high density ultrasonic energy can be concentrated and accurately irradiated on a desired position of a location to be treated.

WO-03/059437 describes a system and method for providing directional ultrasound therapy to skeletal joints, such as spinal joints. WO-03061756 describes a long-term implantable ultrasound therapy system and method is provided that provides directional, focused ultrasound to localized regions of tissue within body joints, such as spinal joints. US-2016/0016012 discloses an external stimulation apparatus using low intensity focused ultrasound, which has a low intensity ultrasound focusing array having a plurality of transducers for outputting low intensity ultrasound beams, and a fixing device to which the low intensity ultrasound focusing array is attached, the fixing device being configured to fix the low intensity ultrasound focusing array to an upper body of a user.

US-2015/0224345 discloses a method of treating a patient having a nerve injury or spinal cord injury or spinal cord lesions, comprising the steps of: activating an acoustic shock wave generator or source to emit acoustic shock waves from a shock wave head; and administering an effective exposure of acoustic shock waves in a pulse or wave pattern having a low energy density less than 1.0 mJ/mm2 per shock wave directly onto a treatment zone in a region extending from the medulla oblongata in the lower brain stem to the lower end of the spinal cord.

US-2005/0020945 discloses an apparatus including an emitter means to deliver acoustic, ultrasonic or vibratory energy in, into or from within a region of the patients brain or spine which contains or is transportably-coupled to cerebrospinal fluid (CSF) or blood capable of bearing or bearing a chemical or biological species, reactant, fragment or byproduct of the disease.

U.S. Pat. No. 8,942,781 describes a percutaneous probe, made in MRI-compatible materials, having: a body percutaneously inserted into the tissue of a patient's body organ having a region to be analyzed, treated and monitored during a single medical procedure; at least one information collection sensing device, treatment application transducers organized in a 360° fashion to emit focused or defocused therapeutic ultra-sound waves.

U.S. Pat. No. 8,977,361 describes an apparatus for the treatment of a brain affection, which comprises at least one implantable generator made of non-ferromagnetic material comprising a casing, and an ultrasound generating treating device positioned into said casing to induce brain affection treatment by emission of ultrasound waves.

US-2015/0231417 discloses a method for treating a spine comprising the steps of: providing a magnetic resonance imaging (MRI) device; identifying a surgical site for treatment of a spinal disorder with the MRI device, the surgical site including a portion of a spine; providing a high intensity focused ultrasound (HIFU) device including a transducer for emitting ultrasound energy; determining parameters of treatment for the surgical site; and applying a dosage of ultrasound energy to the surgical site with the HIFU device for treating the disorder.

US-2013/0178765, US-2013/0281890 and US-2016/0001096 describe methods and systems for non-invasive neuromodulation of the spinal cord utilizing a transducer to deliver pulsed ultrasound energy to up regulate or down regulate neural targets for the treatment of pain and other disease conditions.

There remains the need for a system and a method capable of causing the transient disruption of the blood-spinal cord barrier and/or of the blood-spinal nerve barrier of a vertebrate subject. The specificity of these tissues and their location within the spine vertebrae, especially in the spinal canal, and the need to cause only a transient disruption of the blood-spinal cord barrier and/or of the blood-spinal nerve barrier in the targeted tissues, without damaging the targeted tissues, require a specific system and a specific method not yet available from the prior art.

SUMMARY

The invention relates to an external ultrasound generating treating device to induce spinal cord and/or spinal nerve treatment by emission of ultrasound waves, wherein the ultrasound generating treating device is suitable for external positioning against the back of a patient, said device comprising an array of several ultrasound generating treatment transducers distributed along a longitudinal direction and a lateral direction, wherein the external ultrasound generating device comprises at least two sub-arrays of ultrasound generating treatment transducers, a left sub-array being located on a left lateral side of a central longitudinal axis and a right sub-array being located on a right lateral side of the central longitudinal axis, laterally opposite to the left side.

The external device is characterized in that it comprises a support structure having at least one module comprising a left lateral section holding at least a first left treatment transducer or set of treatment transducers of the left sub-array, and a right lateral section holding at least a first right treatment transducer or set of treatment transducers of the right sub-array, and in that the support structure maintains, in use of the device, a constant distance and a constant relative angular orientation around a longitudinal axis between the first left and first right treatment transducers or set of treatment transducers.

According to other optional features of such implantable device, taken alone or in combination:

The support structure may comprise an adjusting mechanism for adjusting, around a longitudinal axis, a relative angular orientation between the left and right lateral sections of the support structure, so as to adjust the relative angular orientation around the longitudinal axis between the first left and first right treatment transducers or set of treatment transducers.

The adjusting mechanism may comprise an articulation.

The support structure may comprise an adjusting mechanism for adjusting a distance between the left and right lateral sections of the support structure, so as to adjust the distance between the first left and first right treatment transducers or set of treatment transducers.

The adjusting mechanism may comprise a lock for maintaining, in use of the device, a constant distance and a constant relative angular orientation around the central longitudinal axis between the first left and first right treatment transducers or set of treatment transducers.

The left and right lateral sections may have ultrasonic imaging transducers for forming respectively a left and a right image of an emission zone of the treatment transducer or set of treatment transducers held on the same section.

The external ultrasound generating treating device comprises ultrasonic monitoring transducers.

The support structure may comprise several modules arranged successively along the longitudinal direction, each module comprising a left lateral section, holding at least a left treatment transducer or set of treatment transducers of the left sub-array, and a right lateral section, holding at least a right treatment transducer or set of treatment transducers of the right sub-array, and the support structure maintains, in use of the device, a constant distance and a constant relative angular orientation around a longitudinal axis between the respective left and right treatment transducers or set of treatment transducers.

Several modules have each an adjusting mechanism for adjusting, around a longitudinal axis, a relative angular orientation between the respective left and right lateral sections of the support structure, so as to adjust the angular orientation around a longitudinal axis between the first left and first right treatment transducers or set of treatment transducers.

The adjusting mechanisms of several modules may be mechanically connected for simultaneous adjustment.

At least two modules of the support structure may articulated to allow a relative angular movement between the two modules around an axis extending along the lateral direction.

At least two modules of the support structure are articulated through a flexible module connector.

The invention also relates to an apparatus for inducing spinal cord and/or spinal nerve treatment by emission of ultrasound waves, characterized in that it comprises:
an external ultrasound generating treating device having any of the above features;
a generator to supply electricity to the external ultrasound generating treating device;
a controller.

In such apparatus, the ultrasound generating treating external device may comprise left and right lateral sections of the external device having respective ultrasonic imaging transducers for forming respectively a left and a right image of an emission zone of the treatment transducer or set of treatment transducers held on the same section, and the controller may comprise an imaging module connected to the imaging transducers.

The invention also relates to a method for transiently opening the blood-spinal cord barrier and/or the blood spinal nerves barrier in at least one treatment zone of the spinal cord and/or spinal nerves of a patient, said method comprising:
positioning externally against the back of the patient:
at least one left ultrasound generating treatment transducer or set of treatment transducers, having a left emission zone, on a left lateral side of the back of the patient with respect to the spine of the patient, and
at least one right ultrasound generating treatment transducer or set of treatment transducers, having a right emission zone, on a right lateral side of the back of the patient with respect to the spine of the patient, forming at least one left image along a left imaging axis having a set orientation with respect to the left emission zone and one right image along right imaging axis having a set orientation with respect to the right emission zone;

orienting the left and right emission zones according to the left and right images so that the left and right ultrasound emission zones are at least partially superposed on the treatment zone of the spinal cord or on the spinal nerves.

According to other optional features of such method, taken alone or in combination:

Orienting the left and right emission may comprise orienting the treatment transducers or set of treatment transducers according to the left and right images so that the left and right ultrasound emission zones are at least partially superposed on the treatment zone of the spinal cord or on the spinal nerves.

Orienting the left and right emission may comprise controlling the left and right treatment transducers or set of treatment transducers so as to electronically steer the left and right emission zones.

The treatment zone may extend throughout the extension of several vertebrae of the patient.

The method may involve the intravenous injection of an ultrasound contrast agent in the patient's blood circulation system, prior to and/or during the generation of the least one ultrasound treatment beam.

The treatment ultrasound beam has a resonant frequency ranging from 0.5 to 4 MHz, preferably ranging from 0.75 to 2 MHz.

The pressure level of the treatment beam may be determined to obtain a pressure level within the spinal cord and/or spinal nerve tissues between 0.8 MPa and 3.0 MPa.

The applied treatment beam may have a mechanical index (MI) within the spinal cord and/or spinal nerve tissues of from 0.3 to 3.0.

BRIEF DESCRIPTION OF THE DRAWINGS

The device, apparatus and method of the present invention will be further described in detail below with reference to the accompanying drawings showing preferred embodiments of the apparatus of the invention.

In the figures:

FIGS. 3 and 4 represent schematically an example of the positioning of a device according to the invention, comprising several modules, against the back of a patient, respectively in back view and in lateral view;

FIG. 5 represent schematically an enlarged view of a portion of the device of FIG. 3.

DETAILED DESCRIPTION

Figure 1:
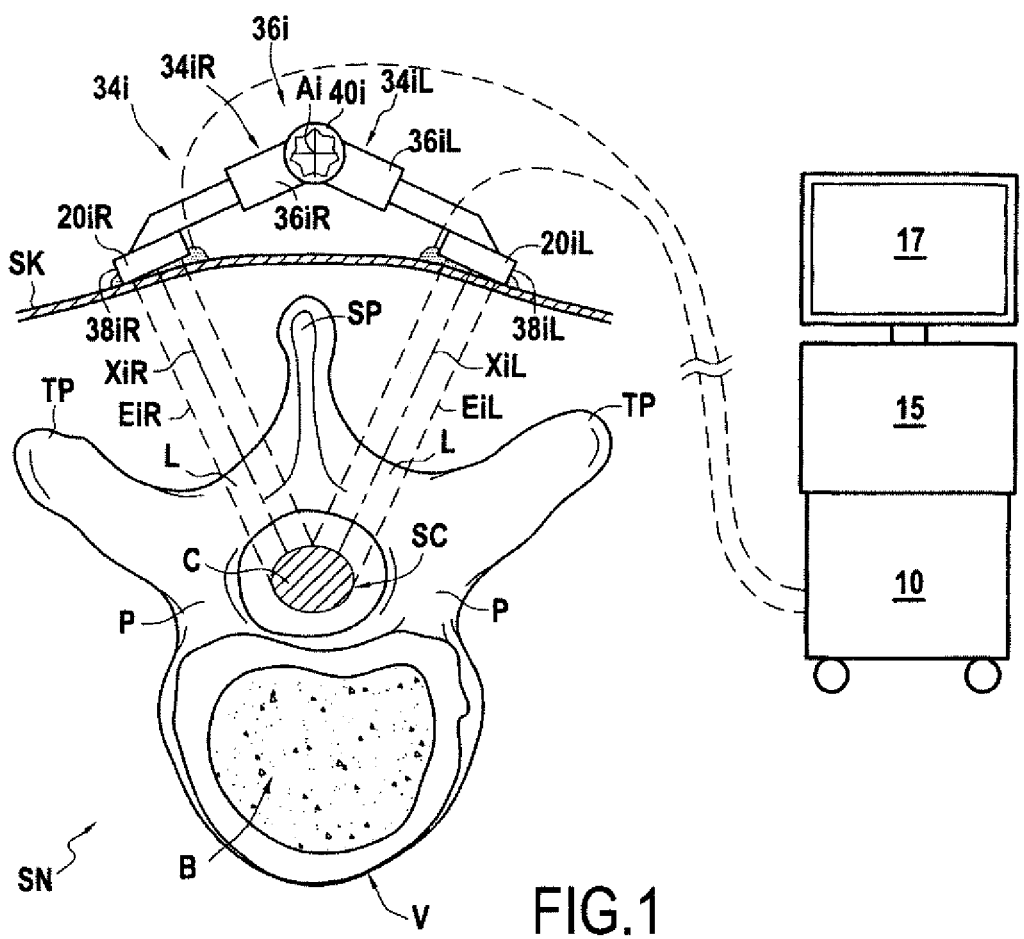
FIG. 1 represents schematically an example of the positioning of a device according to the invention against the back of a patient, in cross-section though a transversal plane of the patient, viewed from the top.

On FIG. 1 are shown the main components of an apparatus to induce spinal cord or spinal nerves treatment by emission of ultrasound waves, comprising an exemplary embodiment of an external ultrasound generating treating device 12 according to the invention.

The apparatus comprises:

an external ultrasound generating treating device 12;

an electrical generator 10 which generates electric signals to be delivered to the transducers of the external ultrasound generating treating device, where the generator may remain external to the body of the patient in use of the apparatus;

a controller 15, also external to the body, for example under the form of a computer, to set and control the working parameters of the generator.

According to an aspect of the invention, the external ultrasound generating treating device 12 is suitable for external positioning against the back of a patient who is awaiting the receipt of, or is receiving medical care or was/is/will be the object of a medical procedure, or is monitored for the diagnosis or the development of a disease. The patient can be any vertebrate subject, especially a mammal and in particular a human i.e., a person of the species *Homo sapiens*.

FIGS. 3 to 5 illustrate schematically such a positioning in the case of a human patient. On those figures, one can see the spine SN of the patient, on the internal side of the skin SK of the back of the patient. The spine SN comprises vertebrae V. In a typical human vertebra, as shown on FIG. 1 in a transverse cross-section perpendicular to the extension of the spine, a vertebra comprises a spinal canal SC portion which is delimited:

towards the front by the vertebra body B, towards the sides by the two pedicles P which join the body B to the two transverse process TP, and towards the rear by the spinous process SP and the two laminas L which join each the spinal process SP to one of the two transverse processes TP.

The spinal cord C is located in the spinal canal and the spinal nerves (not represented) emerge from the spinal cord and extend laterally out of the spinal canal between two vertebrae.

More particularly, the external ultrasound generating treating device 12 is suitable for positioning, preferably directly on the skin, against the back, along the extension of at least a portion of the spine. A coupling agent, such as a gel, may be needed.

In operation, the generator 10 and the external ultrasound generating treating device 12 are to be connected electrically. Such electrical connection could be permanent. However, electrical connection is preferably a cable connection achieved through a connector device of the generator 10 and a connection receiver of the external treating device 12 which can be connected and disconnected, for example in the form of a plug-and-socket connection.

The external ultrasound generating treating device 12 comprises an array of several ultrasound generating treatment transducers distributed along a longitudinal direction and a lateral direction.

The treatment transducers generate focused or unfocused ultrasounds.

The ultrasound generating treatment transducers 20 are preferably chosen into the group formed by piezo-composite elements, piezo-ceramic elements, CMUT elements (Capacitive micro-machined ultrasonic transducers), or PVDF elements (Poly(vinylidene fluoride)). Piezo-composite elements or piezo-ceramic elements usually have a size in the range of 1 to 50 mm in diameter. CMUT elements usually have a size in the range of 10 to 50 μm in diameter. Piezoelectric components are commonly used in the medical field as ultrasound transducers. A given transducer can comprise one or several discrete elements which are activated simultaneously.

The ultrasound treatment transducers have an ultrasound generating resonant frequency which is preferably comprised between 0.5 and 4 Mhz, more preferably between 0.75 and 2 Mhz for achieving transient disruption of the blood-spinal cord barrier and/or of the blood-spinal nerve barrier of the targeted portion of the spinal cord and/spinal nerve(s).

In most commonly used ultrasound generating transducers, the ultrasound energy is generated by virtue of the vibration created in the core of the transducer by an alternating voltage by virtue of a piezoelectric effect or capacitive variation. The transducer is fed with an electric voltage which may have a given frequency or which may have a frequency spectrum which may be decomposed into preferably a limited number of main frequencies. The core of the transducer may thus be designed such that it exhibits at least one inherent resonant frequency.

A resonant frequency of the transducer can be defined as the frequency of the drive signal for which the ratio of the acoustic power output divided by consumed electrical power reaches a maximum (at least within neighbouring frequencies). For a typical piezoceramic transducer, this ratio is typically between 50% and 90% at a resonant frequency. If the electric current fed to the transducer exhibits such frequency, it will induce in the transducer a resonant vibration which will generate ultrasound. If the electric current fed to the transducer exhibits only a frequency or frequencies which lie outside of a resonant range around the resonant frequency, then the acoustic power output will be less than 25% of the power delivered when driven with a given voltage at its resonant frequency.

It must be noted that the term resonant frequency, as used in this text, covers an individual peak resonant frequency, at which the transducer 20 delivers a peak ultrasound field power/intensity for a given electric drive signal power, or a resonant frequency range, around such peak resonant frequency, for which the transducer 20 delivers a ultrasound field power/intensity higher than a minimum field power/intensity, which may be expressed as a percentage of the peak ultrasound field power/intensity.

A transducer may have a given operating frequency by choosing for example its resonant thickness along a given direction along which the ultrasound waves are to be emitted. For example thickness for a 1 MHz transducer for PZ26 material should be at 2 mm along the desired direction of emission.

The frequency content of the electric drive signal can be obtained directly, in case of a simple alternating voltage having one frequency, such as a pure sinusoidal signal. It can also be obtained through Fast Fourier Transform (FFT), as known to the man skilled in the art of signal processing.

It can be noted that, the intensity/power of the ultrasound field generated by a given transducer will depend on the amplitude of the electric drive signal delivered by the generator 10 at the operating frequency.

In use, the external ultrasound generating treating device 12 is intended to be positioned against the back of the patient with its longitudinal direction parallel to the elongation line of the spine, i.e. in the sagittal plane of the patient, and its lateral direction extending perpendicularly to the longitudinal direction, parallel to the axial and coronal planes of the patient.

More precisely, the array of several ultrasound generating treatment transducers comprises at least two sub-arrays of ultrasound generating treatment transducers, a left sub-array being located on a left lateral side of a central longitudinal axis and a right sub-array being located on a right lateral side of the central longitudinal, laterally opposite to the left side.

The external ultrasound generating treating device 12 comprises a support structure 32 having at least one module 34$i$, one of which can arbitrarily be named a first module, each module comprising a left lateral section 34$i$L, holding at least a first left treatment transducer 20$i$L or set of treatment transducers of the left sub-array, and a right lateral section 34$i$R holding at least a first right treatment transducer 20$i$R or set of treatment transducers of the right sub-array. It will be seen that the support structure 32 preferably comprises several modules, preferably several modules 34$i$ having the same features.

The left and right lateral sections 34$i$L, 34$i$R of a module 34$i$ of the support structure 32 preferably comprise each a support member which holds respectively the first left treatment transducer 20$i$L or set of treatment transducers and the first right treatment transducer 20$i$R or set of treatment transducers. The support member of a given module section 34$i$L, 34$i$R and the arrangement of the treatment transducers on that support member are preferably rigid enough so that, in use of the device, i.e. when exposed to the normal forces involved in normal use, there is no movement of the transducers relative to the support member and, if applicable, no relative movement between the set of transducers of a given module section 34$i$L, 34$i$R.

The support structure 32 maintains, in use of the device, a constant distance and a constant relative angular orientation around a longitudinal axis, e.g. the central longitudinal axis Ai of the module 34$i$, between the first left and first right treatment transducers or set of treatment transducers 20$i$L, 20$i$R. In other words, the support structure holds the left and right treatment transducers or set of treatment transducers 20$i$L, 20$i$R rigidly enough to maintain, during use, a constant distance and relative angular orientation between the first left and first right treatment transducers or set of treatment transducers 20$i$L, 20$i$R.

As will be seen, a given module 34$i$ of the support structure 32 may be arranged in the external ultrasound generating treating device 12 so that its central longitudinal axis Ai extends along or parallel to the longitudinal direction of the external ultrasound generating treating device 12.

In use, i.e. at least during the duration of application of an ultrasound treatment beam to the patient as will be described below, the first left and first right treatment transducers or set of treatment transducers 20$i$L, 20$i$R have no relative movement and keep a same relative spatial configuration. This same spatial relative configuration is maintained even in spite of the patient having small movements during the application of the ultrasound treatment beam, including movements due to the patient breathing.

The constant distance is preferably maintained between any two points of the first left and first right treatment transducers or set of treatment transducers 20$i$L, 20R.

An ultrasound generating treatment transducer 20$i$L, 20$i$R can be considered to have a given ultrasound emission zone, typically in the form approximately of a cylinder or a cone in which the intensity of the ultrasound field is significant. For a set of treatment transducers of a given module section 34$i$L, 34$i$R, the combined treatment transducers thereby generate a combined section emission zone, which can be assimilated, for the purpose of the invention, to an emission zone of a combined transducer. For example, in FIG. 1 is shown the case of said field of an external ultrasound generating device 12 having left and right treatment transducers or set of treatment transducers 20iL, 20iR. Each left and right treatment transducers or set of treatment transducers 20iL, 20iR, when properly activated at its operating frequency, delivers an ultrasound field which can be characterized by a border emission envelope EiL, EiR which is shown here as a cylinder or a cone having a central axis XiL, XiR. The border emission envelope of the emission zone EiL, EiR can be defined as the envelope containing all locations where the acoustic pressure of the ultrasound field generated by the corresponding left and right treatment transducers or set of treatment transducers 20iL, 20iR is equal to at least a certain percentage, for example 25%, of the ultrasound field, at the same distance from the transducer, along a direction of maximum acoustic pressure. In real-world examples, the border envelope is not exactly a cylinder or a cone but, for the type of transducers used in the field of medical treatment ultrasound, can be considered as fairly close to a cone, or at least may be comprised in such a cone. Thus, the treatment transducers may have an ultrasound emission zone comprised in a cone having a central emission axis XiL, XiR as its axis of symmetry. Such cone has preferably an opening angle less than 30 degrees.

As can be seen on FIG. 1, the treatment transducers are respectively arranged on their respective module sections so that the emissions zones of the left and right treatment transducers or set of treatment transducers 20iL, 20iR are targeted towards the spinal canal when the external device 12 is positioned along the spine of a patient, against the back the patient. Therefore, the central emission axis XiL, XiR of the corresponding left and right emission zones is preferably perpendicular to the longitudinal direction. In a plane perpendicular to the longitudinal direction, the left and right emission zones are preferably directed so as converge on the spinal canal when the external device 12 is positioned along the spine of a patient, against the back the patient.

The constant distance and relative angular orientation between the first left and first right treatment transducers or set of treatment transducers 20iL, 20iR induces that the emission zones, including the combined emission zone if applicable, of the first left and first right treatment transducers or set of treatment transducers 20iL, 20iR keep a same relative spatial configuration, when the external device 12 is positioned along the spine of a patient, against the back the patient. In other words, in use of the device, the support structure is rigid enough between the left and right sections of a given module in order that the support structure does not deform when subject to the normal forces endured during normal use of the device.

For example, as in the shown embodiment, each section of the module may comprise a support member having a rigid arm 36iL, 36iR extending laterally, the two arms 36iL, 36iR being connected at a respective proximal end, and a respective transducer bracket 38iL, 38iR rigidly connected at their respective distal ends. The brackets may be in the form of rigid plate like elements. Such brackets preferably extend along a limited width according to the lateral direction, for example less than 5 cm, preferably less than 3 cm. Such brackets preferably extend along a length according to the longitudinal direction which is preferably comprise between 1 cm and 15 cm, preferably between 3 cm and 10 cm. The arms 36iL, 36iR may form an arch extending laterally between the transducer brackets 38iL, 38iR. The brackets are preferably spaced apart with their facing edges laterally distant by at least 1 cm, preferably at least 3 cm.

In some embodiments, for a given module 34i of the support structure 32, the relative sections 34iL, 34iR have a non-adjustable relative spatial configuration, including a constant distance and relative angular orientation. Such non-adjustable relative spatial configuration 34iL, 34iR of the relative sections 34iL, 34iR may be set once and for all, for example at the moment of manufacture of the external device 12. In such a case, the the two arms 36iL, 36iR of pertaining to the respective sections of a module 34i may be joined at their proximal end so as to form a single rigid and non-adjustable part, for example in form of a rigid arch.

Such a non-adjustable module is thus then designed in view of predefined geometry of an expected patient's anatomy, so that the left and right emission zones are preferably directed so as converge on the spinal canal when the external device 12 is positioned along the spine of a patient, against the back the patient.

However, in some embodiment of the invention, the support structure of a given module 34i may comprise an adjusting mechanism 36i for adjusting the relative spatial configuration of the left and right sections 34iL, 34iR of the module 34i. This allows for a more precise targeting of the ultrasound treatment beam on the spinal cord and/or a spinal nerve.

Such adjustment may include the adjustment, around a longitudinal axis, e.g. the central longitudinal axis Ai of the module 34i, of a relative angular orientation between the left and right lateral sections 34iL, 34iR of the support structure 32, so as to adjust the angular orientation around the central longitudinal axis Ai between the first left and first right treatment transducers or set of treatment transducers 20iL, 20iR.

The adjusting mechanism may comprise an adjustment articulation 36i.

In some embodiments, a single adjustment articulation 36i may be provided between the two sections 34iL, 34iR of a given module 34i. As in the example, such single articulation 36i may be located centrally, at the proximal end of the arms 36iL, 36iR.

In some embodiments, an adjustment articulation 36i may be provided in each of the two sections 34iL, 34iR of a given module 34i, for example between the bracket 38iL, 38iR and the distal end of the corresponding arm 36iL, 36iR.

An adjustment articulation 36i may comprise a mechanical articulation comprising two rigid parts having a relative motion along respective sliding surfaces, such as a pivot or ball joint connection.

An adjustment articulation 36i may be of the type having two or three rotational degrees of freedom, for example around two or three perpendicular articulation axes, including the central longitudinal axis Ai of the module 34i or another longitudinal axis parallel thereto.

However, as shown in the depicted embodiments, an adjustment articulation may be of the type having only one degree of freedom, for example around only a longitudinal axis, e.g. the central longitudinal axis Ai, with no other possible rotational movement between the two sections 34iL, 34iR of the module 34i.

Similarly, the support structure 32 may comprise an adjusting mechanism for adjusting a distance, for example along a lateral direction of the module, between the left and right lateral sections 34iL, 34iR of the support structure of the module 34i, so as to adjust the distance between the first left and first right treatment transducers or set of treatment transducers of that module 20iL, 20iR. For example, in the example shown, the arms of the support member in each section may be telescopic and adjustable in length. Alternately, the brackets could be attached to the arms in an adjustable manner along the extension of the arm.

Preferably the adjusting mechanism 36*i* comprises a lock 40*i* for maintaining, in use of the device, a constant distance and a constant relative angular orientation around the central longitudinal axis between the first left and first right treatment transducers or set of treatment transducers. The lock may comprise a tightening screw tightening the adjustment mechanism in a desired position. The lock may thus allow locking of the adjustment mechanism in any position in a range of positions, to allow continuous adjustment of the relative spatial configure of the two sections of the module 34*i* with a range of relative spatial configurations. The lock may comprise indents allowing locking only in predefined spatial configurations.

The optimum relative spatial configuration of the left and first right treatment transducers or set of treatment transducers 20*i*L, 20*i*R of a given module is dependent on the expected anatomy of a patient.

For an external ultrasound generating treating device 12 intended for use on an adult human, a range of adjustment of the angular orientation, around the central longitudinal axis Ai, between the first left and first right treatment transducers or set of treatment transducers 20*i*L, 20*i*R, is preferably of at least 30 degrees, preferably of at least 60 degrees.

For an external ultrasound generating treating device 12 intended for use on an adult human, a range of adjustment of the distance, along a lateral direction of the module, between the first left and first right treatment transducers or set of treatment transducers 20*i*L, 20*i*R, is preferably of at least 50 millimeters, preferably of at least 100 mm.

Having an optimal spatial configuration of the left and right treatment transducers or set of treatment transducers, and maintaining this optimal spatial orientation is an important aspect. An optimal spatial configuration is for example achieved when the left and right emissions zones of the left and right treatment transducers or set of treatment are at least partially superposed on the treatment zone of the spinal cord or on the spinal nerves of the patient. Even more optimal is to have the left and right emissions zones transducers intersecting a portion of minimum thickness of the lamina of the vertrebrae before hitting the the spinal cord or on the spinal nerves of the patient.

In non-adjustable modules, a proper design allows an adaptation of the device to an average patient anatomy, already allowing in most cases that a good portion of the left and right emission zones avoid at least the spinous process and the transverse processes of the vertebrae.

Having transducers coming from both the left and the right side and targeted at the same treatment zone of the spinal cord or on the spinal nerves of the patient allows a better handling of the diffraction effects.

However, modules having an adjustment mechanism allow a perfect adaptation of the external device to the patient's real anatomy, and thus allows the most optimal ultrasound treatment conditions. Once an optimal adjustment is determined and set, it is maintained during the used of the device, for example by locking the adjusting mechanism with a lock.

In some embodiments, the left and right lateral sections 34*i*L, 34*i*R of a given module 34*i* of the external ultrasound generating treating device 12 may have ultrasonic imaging transducers 42*i*L, 42*i*R for forming respectively a left and a right image of an emission zone of the treatment transducer or set of treatment transducers 20*i*L, 20*i*R held on the same section. Such images are typically digital images obtained from the ultrasound information collected by the ultrasonic imaging transducers 42*i*L, 42*i*R. The imaging transducers may be of any suitable conventional type known to the skilled man in the art. They may have an operating frequency comprised between 200 KHzz and 20 GHz, preferably from above 2 GHz to 20 GHz. Each ultrasonic imaging transducer 42*i*L, 42*i*R may be formed of one or several individual transducers. They may be held by the same support member as the treatment transducers, for example the brackets 38*i*L, 38*i*R. The relative configuration of the ultrasonic imaging transducers 42*i*L, 42*i*R with respect of to the treatment transducer or set of treatment transducers 20*i*L, 20*i*R held on the same section is preferably fixed, but may be different to the schematic shown on FIG. 2.

The external ultrasound generating treating device 12 may comprise ultrasonic monitoring transducers 44*i*L, 44*i*R, for example wideband ultrasonic transducers. Monitoring transducers may be flexible membrane transducers. Monitoring transducers are preferably able to pick-up an ultrasound signal over a wide frequency range, ideally between 50 kHz and 50 Mhz. Such monitoring transducers may be tailored and used for monitoring cavitation due to the ultrasonic treatment.

A module 34*i* could be of limited extension the longitudinal direction, for example corresponding to the length of a single vertebra of a patient and adapted to treat a treatment zone of comparable extension. It could be longer along that direction, for example corresponding to the length of several vertebrae of a patient and adapted to treat a treatment zone of comparable extension.

An external ultrasound generating treating device 12 may comprise a single module as described above.

Preferably, as shown on FIGS. 2 to 5, the support structure 32 comprises several modules 34*i* arranged successively along the longitudinal direction, each module 34*i* having one or several of the above features. Each module 34*i* comprises a left lateral section holding at least a left treatment transducer or set of treatment transducers of the left sub-array, and a right lateral section holding at least a right treatment transducer or set of treatment transducers of the right sub-array. As described above, the support structure maintains, in each module 34*i*, in use of the device, a constant distance and a constant relative angular orientation around the central longitudinal axis of the respective module between the respective left and first treatment transducers or set of treatment transducers of said module 34*i*.

All the modules 34*i* could have the same size. However, it can be provided that different modules 34*i* could be of different sizes depending on their location along the longitudinal direction of the external device 12.

All of the modules 34*i* could have the same features. However, it can be provided that different modules 34*i* could have a different set of features amidst the above described features.

Preferably several modules 34*i* have each an adjusting mechanism 34*i* for adjusting, around their respective central longitudinal axis, a relative angular orientation between the respective left and right lateral sections of the support structure, so as to adjust the angular orientation around the central longitudinal axis between the first left and first right treatment transducers or set of treatment transducers of that module 34*i*.

In such a case, the adjusting mechanisms 36*i* of several modules 34*i* may be advantageously mechanically connected for simultaneous adjustment. The simultaneous adjustment of the several modules 34*i* can follow a predefined relative variation.

In an external ultrasound generating treating device 12 having a support structure 32 comprising several modules 34*i* arranged successively along the longitudinal direction, at least two modules 34*i* of the support structure 32 may be articulated to allow a relative angular movement between the two modules around an axis extending along the lateral direction. Such an example is represented on FIGS. 3 to 5. Upon positioning of the external device against the back of a patient, such device can thus adapt and conform to the shape of the spine, as particularly visible on FIG. 4.

Two successive modules 34*i* may be articulated though a single or several inter-module articulation(s) 46, arranged in parallel or in series.

Two successive modules 34*i* may be articulated with only one degree of freedom, for example around only one laterally extending axis Bi, with no other possible rotational movement between the two modules 34*i*. However, two successive modules 34*i* may preferably be articulated with several degrees of freedom. Preferably the modules are articulated so that some degree of twisting around the longitudinal axis is also possible, in addition to an articulation around the lateral axis. Furthermore, the connection between two modules preferably additionally allows a relative displacement, along a direction perpendicular to the lateral and longitudinal directions, of two facing laterally extending edges of two consecutives modules.

An articulation may comprise a mechanical articulation comprising two rigid parts having a relative motion along respective sliding surfaces, such as a pivot or ball joint connection.

However, as shown in the depicted embodiments, at least two modules 34*i* of the support structure 32 are articulated through one or several flexible module connector 46. A flexible module connector 46 may be a sheet of flexible material, extending preferably in a longitudinally and laterally extending plane, or a cable, extending preferably along the longitudinal direction. A flexible module connector 46 may be elastic along the longitudinal direction, or to the contrary it may be inelastic so as to define a set maximum distance between two consecutive modules 34*i* along the longitudinal direction.

In the shown embodiment, the support structure of the external device is symmetrical with respect to a plane of symmetry which extends longitudinally and perpendicularly to the lateral direction. In use, this plane of symmetry is preferably aligned with the spine of the patient.

The left and right sections of a module are each connected respectively to the left and right sections of consecutive modules along the longitudinal direction by a respective flexible module connector 46, here under the form of a sheet of flexible material, extending preferably in a longitudinally and laterally extending plane. The flexible module connectors 46 between two successive modules are here arranged in parallel, spaced apart along the lateral direction on each side of longitudinal axis.

Each flexible module connector 46 has a length along the longitudinal direction which is preferably of at least 10 mm, more preferably at least 20 mm, to allow sufficient flexibility and relative movement between two consecutive modules.

The external ultrasound generating treating device 12 also comprises an electrical connection network for connecting the ultrasound generating transducers 20 to the generator 10 delivering electric drive signals. The electric connection network may comprise one or several electrically independent electric connection circuits, where it will be understood that a given electric connection circuit is a circuit where a common electric drive signal is circulating. An independent electric connection circuit may be used to drive a single treatment transducer or may be used to drive a group of treatment transducers. Each independent electric connection circuit will have its own independent electric connection to the generator 10 and the generator may deliver separate and different electric drive signals to each independent electric connection circuit. For example it can be provided that each module has its own independent electric connection circuit, which may be shared between its left and right sections. Independent electric connection circuit may be useful for addressing possible impedance variation between transducers.

In any case, imaging transducers and/or monitoring transducers, if present, would preferably have their own separate electric connection circuit.

Preferably, the external ultrasound generating treating device 12 is made of non-ferromagnetic materials, preferably MRI compatible materials.

The generator 10 is adapted for delivering electric drive signals to be delivered to the ultrasound generating treatment transducers 20 of an associated ultrasound generating treating device 12. The generator typically comprises an alternating voltage generator able to generate an electric signal, for example a sinusoidal electric voltage signal. One example of a generator system that can be used with the inventive device may include a system that integrates signal generation, amplification, and control into a single unit. However, a generator system can also comprise one or several individual components performing one or more of these functions. For example, the generator can include an HP/Agilent 33120 function generator. If needed, it can also include for example one or more of an ENI 240L Broadband RF amplifier, of a Rhode and Schwarz RF power meter, and/or external computer controlling equipment over GPIB/Serial/USB interfaces.

Therefore, the controller 15 may comprise a computer. A computer human/machine interface 17, for example a keyboard, and/or mouse and/or a display and/or a touchscreen interface, can be provided to control the system and give the user feedback. A radiofrequency board that generates the RF signal and amplifies it may be provided, as well as a coupler to measure the delivered RF power, and matching components to tune the generator output to the impedance of the ultrasound elements. Preferably, the generator 10 may be of a type capable to deliver 25-100 W peak RF power, capable of sending burst lengths with durations of 1 microsecond to continuous mode, and capable of sending bursts within the frequency range of 200 kHz to 2 MHz. Such a system can be controlled to send pulses with variable frequency and duty cycles for durations of approximately 2-5 minutes. The generator may be a class A/B RF system, which means that it is capable of generating nearly pure sinusoidal signals, but this may make the system rather large. In some embodiments, the generator could be a class D system, which tends to generate signals that are square wave on the output.

Figure 2:
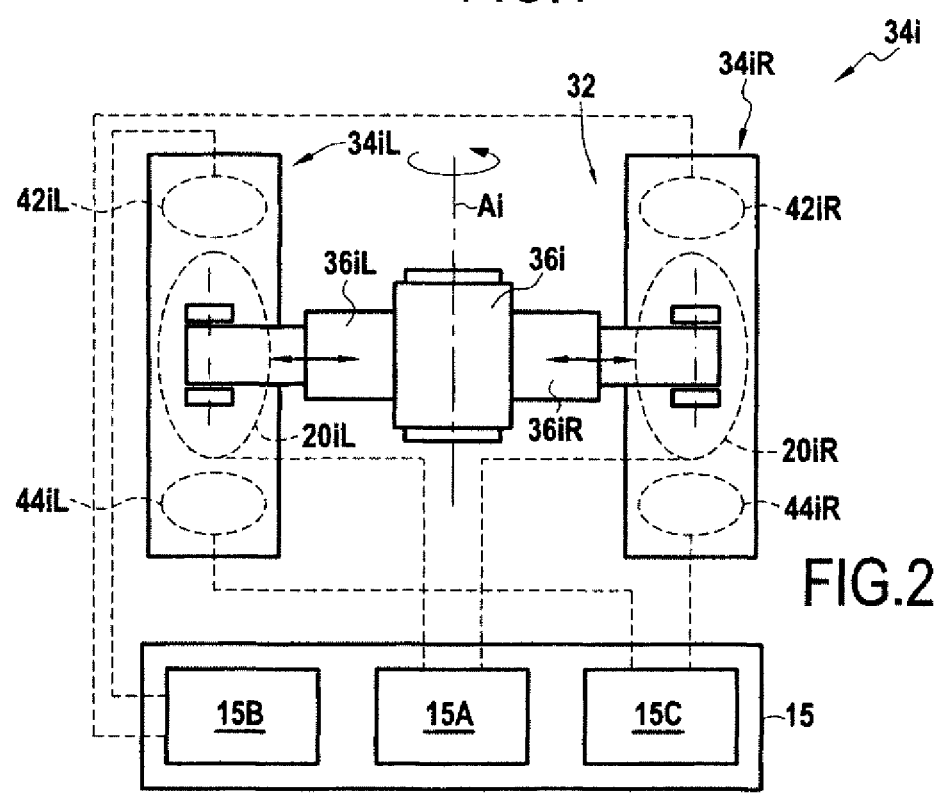
FIG. 2 represents schematically an embodiment of a module of device according to the invention.

As seen on FIG. 2, the controller 15 may comprise a treatment control module 15A for controlling the generator in view of providing the adequate electric drive signals to the treatment transducer or set of treatment transducers 20*i*L, 20*i*R of the external ultrasound treating device 12.

The controller 15 may also comprise an imaging module 15B connected to the imaging transducers 42*i*L, 42*i*R of the external ultrasound treating device 12, if provided with such imaging transducers. The imaging module 15B may be configured to display one or several images on a display 17, and/or to provide data extracted from a controller performed analysis of the images.

The controller 15 may also comprise a monitoring module 15C connected to the monitoring transducers 44*i*L, 44*i*R of the external ultrasound treating device 12, if provided with such monitoring transducers. The monitoring module 15C may be configured to display one or several images on a display 17, and/or to provide data extracted from a controller performed analysis of the ultrasound signal collected by the imaging transducers.

According to another aspect of the invention, it is provided a method for transiently opening the blood-spinal cord barrier and/or the blood spinal nerves barrier in at least one treatment zone of the spinal cord and/or spinal nerves of a patient.

In the context of the invention, the terms "disrupting", "opening" or "increasing the permeability" of the BSCB or BSNB are used interchangeably to refer to an increased susceptibility of the BSCB or BSNB to the passage of molecules therethrough that occurs without detectable damaging of the spinal cord or spinal nerve tissue.

In the context of the invention, a "transient" opening refers to a reversible opening occurring preferably for more than 1 hour, the BSCB or BSNB returning after that to its initial state (i.e., the BSCB or BSNB state before the application of the first ultrasound treatment beam).

In some embodiments, the BSCB or BSNB opening occurs for a period of time from 1 to 48 hours, preferably from 5 to 24 hours, more preferably from 6 to 10 hours. In some embodiments, the BSCB or BSNB opening occurs for approximately 8 hours.

In some embodiments, the BSCB or BSNB disruption is delimited, i.e., occurs solely in a target region of the BSCB or BSNB. For instance, only a region of the BSCB or BSNB surrounding damaged spinal cord or spinal nerve tissue, such as a tumor, is targeted. In other embodiments, the BSCB or BSNB disruption is generalized.

The disruption may be easily confirmed and/or evaluated by magnetic resonance imaging (MRI). For example, a gadolinium-based magnetic resonance (MR) contrast agent such as Dotarem® (gadoterate meglumine, Guerbet USA), which does not normally cross the BSCB or BSNB, can be used to visualize the region of BSCB or BSNB disruption. When the agent is injected in a patient, a T1w MR sequence can be used to visualize regions of hypersignal and therefore visualize the effect of BSCB or BSNB disruption by ultrasound. BSCB or BSNB disruption typically leads to a change of 5-10% or more in MR signal enhancement after contrast agent administration. With the invention, a change of more than 25%, preferably more than 50% in MR signal enhancement after contrast agent administration is contemplated. In addition, dynamic contrast enhanced (DCE) MR imaging techniques can be used to calculate the permeability of the BSCB or BSNB and to quantify the magnitude of the permeability enhancement after ultrasound treatment.

The method can be used for delivering substances into targeted spinal cord or spinal nerve tissue of the subject and/or for treating a the spinal cord or spinal nerve disease.

The method can be used to treat various physiological disorders which induce different forms of pathologies including;
- spinal degenerative pathologies, such as amyotrophic lateral sclerosis (ALS)
- spinal cord tumor diseases, such as spinal astrocytomas
- spinal inflammatory pathologies, such as multiple sclerosis, etc. . . . .

It can also be used to improve the repair and/or rehabilitation treatments of the spinal cord and/or spinal nerve(s), for example for hemiplegia and paraplegia, including with cell transplant and/or stem cell regeneration.

The method preferably comprises positioning externally against the skin of the back of the patient:
- at least one left ultrasound generating treatment transducer or set of treatment transducers, having a left emission, on a left lateral side of the back of the patient with respect to the spine of the patient, and
- at least one right ultrasound generating treatment transducer, having a right emission zone, on a right lateral side of the back of the patient with respect to the spine of the patient.

Such method can thus be implemented with an external ultrasound generating treating device 12 as described above.

As explained above, it can be considered that each treatment transducer or set of treatment transducers has an ultrasound emission zone comprised in a cone having a central emission axis as its axis of symmetry.

The method further comprises forming at least one left image along a left imaging axis having a set orientation with respect to the left emission zone and one right image along a right imaging axis having a set orientation with respect to the right emission zone of the left and right treatment transducers or set of treatment transducers. The imaging axis can be the axis joining the center of the imaging transducer or set of imaging transducers to the center of the object which is imaged by the imaging transducer or set of transducers. Such set orientation may be obtained by having a left and right imaging axis corresponding respectively to the left and right central emission axis of the left and right emission zones.

Advantageously, the method provides for orienting left and right emission zones according to the left and right images so that the left and right ultrasound emission zones are at least partially superposed on the treatment zone of the spinal cord or on the spinal nerves. Of course, such method is most conveniently implemented with an external device as described above wherein the support structure of a given module 34i comprise an adjusting mechanism 36i for adjusting the relative spatial configuration of the left and right sections 34iL, 34iR of the module 34i. Indeed, adjustment of the left and right sections 34iL, 34iR of the module 34i is made simply and precisely thanks to the adjustment mechanism, before or at the beginning of the treatment, and the relative configuration is reliably maintained during the treatment.

However, even in the case of an external device having one or several modules not having such adjusting mechanism, but having a left and a right set of treatment transducers, it is also possible to orient the left and right emission zones. In such a case, it is possible to orient the left and right emission zones by controlling the left and a right set of transducers so as to electronically steer the left and right emission zones. Such technique is conventionally called "electronic beam steering". Such technique can involve introducing time delays between the electric drive signals sent to the individual treatment transducers within respectively the left and right sets of treatment transducers. The time delays may be computed to steer the beam in one direction or the other. In any case, electronic beam steering can also be implemented with external devices having an adjusting mechanism according to the invention, thus in addition to the adjustment of the relative angular orientation between the left and right lateral sections of the support structure.

Even more preferably, such method is most conveniently implemented with an external device as described above wherein the support structure of a given module 34i comprise an adjusting mechanism 36i for adjusting the relative spatial configuration of the left and right sections 34*i*L, 34*i*R of the module 34*i*, and wherein the left and right lateral sections 34*i*L, 34*i*R of a given module 34*i* of the external ultrasound generating treating device 12 have ultrasonic imaging transducers 42*i*L, 42*i*R for forming respectively a left and a right image of an emission zone of the treatment transducer or set of treatment transducers 20*i*L, 20*i*R held on the same section. With such a device, there is a direct and fixed correlation between the orientation of the emission and zone and the orientation of the imaging axis held by a same section. Therefore, superposition of the left and right emission zones can be achieved simply by adjusting the relative spatial configuration of the left and right sections 34*i*L, 34*i*R of the module 34*i*, and by comparing the left and right images until a predefined correlation between the two images is obtained, which, by construction of the device, will be known to correspond to a superposition of the emission zones on a desired target location, e.g. on the spinal canal.

For example it is possible to construct the apparatus so that, when the spinal canal appears in the center of each left and right image, then the practitioner knows that the left and right emission zones are at least partially superposed on the treatment zone of the spinal cord or of the spinal nerves.

In a method as above, the treatment zone may extend throughout the extension of several vertebrae of the patient. This is most conveniently implemented with an external device as described above wherein the support structure 32 comprises several modules 34*i* arranged successively along the longitudinal direction, the external device being positioned so that its longitudinal direction is parallel to the extension of the spine of the patient.

The method comprises the application to the treatment zone of the spinal cord and/or spinal nerves of the patient of at least one ultrasound treatment beam. This can be achieved by proper activation of the treatment transducer or set of treatment transducers 20*i*L, 20*i*R of an external device 12 as described above. The use of such a device allows for a very precise control of the ultrasound energy and power delivered to the targeted spinal cord and spinal nerve tissues. It also allows a precise targeting of the treatment zone, with the possibility to precisely control the extension of such treatment zone where the ultrasound treatment beam is effectively applied.

The terms "ultrasound beam", "ultrasound wave" and "ultrasound" are used indifferently for designating sound waves with frequencies higher than 20 kHz. However the ultrasound treatment beam has preferably an ultrasound frequency ranging from 0.5 to 4 MHz, more preferably ranging 0.75 to 2 MHz.

The method preferably involves the injection of an ultrasound contrast agent in the patient's blood circulation system, prior to and/or during the generation of the least one ultrasound treatment beam.

The term "ultrasound contrast agent" is used herein to refer to a substance (solid, liquid or gas) that is able to enhance the contrast between the region containing the agent and the surrounding tissue in an ultrasound image. Advantageously, the ultrasound contrast agent corresponds to small bubbles of a gas, termed "microbubbles," with an average diameter between 1 µm and 10 µm. Said microbubbles oscillate and vibrate when a treatment ultrasound beam is applied and may reflect ultrasound waves. The ultrasound contrast agent is generally injected intravenously into the blood stream in the patient's blood circulation system, wherein it remains for a limited period of time.

The ultrasound contrast agent may be administered by injection, preferably by systemic injection. Examples of systemic injections include intravenous, subcutaneous, intramuscular, intradermal, intra vitreal and intraperitoneal injection, or perfusion.

Preferably, the ultrasound contrast agent is administered as a bolus just before the ultrasound treatment beam application. More preferably, the ultrasound contrast agent is administered between 0 and 60 minutes before, and/or during the ultrasound treatment beam application. When successive ultrasound treatment beams are applied, the ultrasound contrast agent is preferably delivered only once, just before the first ultrasound treatment beam application of the cycle, though it may be delivered at activation of each US beam, or by a continuous infusion through the activation of successive ultrasound treatment beams.

According to the invention, the ultrasound contrast agent may contain gaseous bubbles, a high concentration of gas, solid particles configured to vaporize in response to ultrasound, liquid configured to vaporize in response to ultrasound, micro particles configured to act as cavitation sites, solid particles having higher acoustic impedance than tissue in the desired region, and/or liquid with a high acoustic absorption coefficient.

In some embodiments, the ultrasound contrast agent is a microbubble contrast agent, preferably selected from the group consisting of sulphur hexafluoride microbubbles (SonoVue®), microbubbles made of an albumin shell and octafluoropropane gas core (Optison®), perflexane microbubbles encapsulated in an outer lipid shell (Imagent®), microbubbles made of octafluoropropane gas core encapsulated in an outer lipid shell (Definity®), or perfluorobutaine and nitrogen gas encapsulated in a lipid shell (BR38—Schneider et al., 2011). Preferably, the ultrasound contrast agent consists of sulphur hexafluoride microbubbles. Microbubbles may contain a drug and/or a nanoparticle which may be delivered in situ when the microbubbles are exposed to the ultrasound treatment beam.

The microbubbles may have a mean diameter in a range from 1 µm to 10 µm. In some embodiments, the microbubbles have a mean diameter in a range from 4 µm to 5 µm. In some other embodiments, the microbubbles have a mean diameter in a range from 2 to 6 µm. In some embodiments, the microbubbles have a mean diameter of approximately 7 µm, 6 µm, 5 µm, 4 µm, 3 µm or 2 µm. In a particular embodiment, the microbubbles have a mean diameter of approximately 2.5 µm.

In some embodiments, the dose of ultrasound contrast agent ranges between 0.05 and 0.15 ml/kg based on the total weight of the subject. Preferably, the dose of ultrasound contrast agent is approximately 0.1 ml/kg. In a particular embodiment, the maximum dose of ultrasound contrast agent is up to 10 ml.

Preferably, the pressure level of the ultrasound treatment beam applied to the spinal cord or spinal nerve tissues is comprised between 0.8 MPa and 3.0 MPa. Advantageously, the ultrasound treatment beams are applied within a pressure range of 0.8 MPa to 2.5 MPa, more preferably within a pressure range of 0.8 MPa to 2.00, even more preferably within a pressure range of 0.8 MPa to 1.9, such as within a pressure range of 0.8 MPa to 1.5 MPa, within a pressure range of 1.1 MPa to 1.5 MPa. In a particular embodiment, the ultrasound treatment beams are applied with a pressure level of 1.25 MPa. In another embodiment, the ultrasound treatment beams are applied with a pressure level of 1.5 MPa. In a further embodiment, the ultrasound treatment beams are applied with a pressure level of 1.9 MPa. In the context of the invention, the "pressure level" refers to the maximum acoustic pressure measured in the acoustic field of the device in water. It is believed that such pressure levels may be applied in a safe manner to human's spinal cord and/or spinal nerve, i.e., no detected damages of spinal cord and/or spinal nerve tissue should be observed.

In the context of the invention, the value of the pressure level corresponds to the value onto the spinal cord and/or spinal nerve tissue. The pressure emitted by the device may differ, to take into account potential attenuation of intervening tissues and/or vertebra bone reverberation. One skilled in the art will be able to adapt the value of the pressure level coming out of the emitter to obtain the required pressure level onto the spinal cord and/or spinal nerve. Monitoring of the treatment zone with ultrasonic monitoring transducers can be used for checking the effective value of the pressure level in situ during the treatment.

Preferably, the applied ultrasound treatment beam to the spinal cord or spinal nerve tissues has a mechanical index (MI) of approximately from 1 to 3.00, and preferably in the range of 1.05 to 1.8 in the case of a 1 MHz ultrasound treatment beam. In the context of the invention, the MI refers to the peak negative pressure in situ (MPa) divided by the square root of the frequency (MHz).

Preferably, the ultrasound treatment beam is a pulsed beam. In the context of the invention, a "pulse" refers to a continuous burst, without interruption, of sinusoidal waves that may comprises several cycles.

In some embodiments, the method comprises the application one or more pulses, or bursts, comprising from 100 to 100,000 successive cycles, preferably from 1,000 to 75,000, more preferably from 10,000 to 50,000, even more preferably from 20,000 to 30,000. In a particular embodiment, the method comprises the application of pulses of 25,000 successive cycles. In some embodiments, the mean burst duration of an ultrasound treatment emission (i.e., the mean time from the start of a pulse to the end of that pulse) is between 10 msec. and 100 msec., preferably between 15 msec. and 50 msec., more preferably between 20 msec. and 30 msec., even more preferably approximately 25 msec.

The delay between two successive pulses is preferably from 30 msec. to 1000 msec. In a particular embodiment, the delay between two successive pulses is approximately 975 msec.

Advantageously, the successive pulses are applied within a total duration from 1 to 20 minutes. In a particular embodiment, the successive pulses are applied within a total duration that does not exceed 10 minutes, preferably 5 minutes. In a particular embodiment, the successive pulses are applied within a total duration of 150 seconds.

In a particular embodiment, pulses of 25,000 cycles are applied to the subject, at a pulse repetition frequency (PRF) of 1 Hz, every 1000 msec. with a pressure level of 1.1 MPa and a burst duration of about 23 msec. for a total duration of 150 seconds.

The invention claimed is:

1. An external ultrasound generating treating device (12) to induce spinal cord and/or spinal nerve treatment by emission of ultrasound waves, wherein the ultrasound generating treating device (12) is suitable for external positioning against a back of a patient, said ultrasound generating treating device comprising an array of several ultrasound generating treatment transducers (20*i*L, 20*i*R) distributed along a longitudinal direction and a lateral direction, wherein the external ultrasound generating device comprises at least two sub-arrays of ultrasound generating treatment transducers, a left sub-array (20*i*L) being located on a left lateral side of a central longitudinal axis (Ai) and a right sub-array (20*i*R) being located on a right lateral side of the central longitudinal axis (Ai), laterally opposite to the left side, characterized in that the ultrasound generating treating device comprises a support structure (32) having several modules (34*i*) arranged along the longitudinal direction, each of the several modules comprising a left lateral section (34*i*L) holding at least a left set of treatment transducers of the left sub-array, and a right lateral section (34*i*R) holding at least a right set of treatment transducers of the right sub-array, in that the support structure (32) maintains, in use of the ultrasound generating treating device, a constant distance and a constant relative angular orientation around the central longitudinal axis (Ai) between the left and right set of treatment transducers (20*i*L, 20*i*R), in that each of the several modules comprises an adjusting mechanism (36*i*) comprising an articulation for adjusting, around the longitudinal axis (Ai), a relative angular orientation between the left and right lateral sections (34*i*L, 34*i*R) of the support structure, so as to adjust a relative angular orientation around the central longitudinal axis (Ai) between the left and right sets of treatment transducers (20*i*L, 20*i*R), in that each of the several modules comprises an adjusting mechanism (36*i*) for separately adjusting a distance between the left and right lateral sections of the support structure (34*i*L, 34*i*R), so as to adjust the distance between the left and right sets of treatment transducers (20*i*L, 20*i*R), in that the adjusting mechanism comprises a lock (40*i*) for maintaining, in use of the ultrasound generating treating device, a constant distance and a constant relative angular orientation around the central longitudinal axis between the left and right sets of treatment transducers (20*i*L, 20*i*R), and in that the left and right lateral sections (34*i*L, 34*i*R) have ultrasonic imaging transducers (42*i*L, 42*i*R) for forming respectively a left and a right image of an emission zone of the left and right sets of treatment transducers (20*i*L, 20*i*R) held on respective sections (34*i*L, 34*i*R), wherein the adjusting mechanisms (36*i*) of each of the several modules (34*i*) are mechanically connected for simultaneous adjustment.

2. The external device according to claim 1, characterized in that the external ultrasound generating treating device comprises ultrasonic monitoring transducers (44*i*L, 44*i*R).

3. An apparatus for inducing spinal cord and/or spinal nerve treatment by emission of ultrasound waves, comprising:

the external ultrasound generating treating device (12) according to claim 1;

a generator (10) to supply electricity to the external ultrasound generating treating device; and a controller (15).

4. The apparatus according to claim 3, characterized in that the left and right lateral sections (34*i*L, 34*i*R) of the external ultrasound generating treating device (12) have ultrasonic imaging transducers (42*i*L, 42*i*R) for forming respectively a left and a right image of an emission zone of the left and right sets of treatment transducers (20*i*L, 20*i*R) held on respective sections (34*i*L, 34*i*R), and in that the controller (15) comprises an imaging module (15B) connected to the imaging transducers.

5. An external ultrasound generating treating device (12) to induce spinal cord and/or spinal nerve treatment by emission of ultrasound waves, wherein the ultrasound generating treating device (12) is suitable for external positioning against a back of a patient, said ultrasound generating treating device comprising an array of several ultrasound generating treatment transducers (20iL, 20iR) distributed along a longitudinal direction and a lateral direction, wherein the external ultrasound generating device comprises at least two sub-arrays of ultrasound generating treatment transducers, a left sub-array (20iL) being located on a left lateral side of a central longitudinal axis (Ai) and a right sub-array (20iR) being located on a right lateral side of the central longitudinal axis (Ai), laterally opposite to the left side, characterized in that the ultrasound generating treating device comprises a support structure (32) having several modules (34i) arranged along the longitudinal direction, each of the several modules comprising a left lateral section (34iL) holding at least a left set of treatment transducers of the left sub-array, and a right lateral section (34iR) holding at least a right set of treatment transducers of the right sub-array, in that the support structure (32) maintains, in use of the ultrasound generating treating device, a constant distance and a constant relative angular orientation around the central longitudinal axis (Ai) between the left and right set of treatment transducers (20iL, 20iR), in that each of the several modules comprises an adjusting mechanism (36i) comprising an articulation for adjusting, around the longitudinal axis (Ai), a relative angular orientation between the left and right lateral sections (34iL, 34iR) of the support structure, so as to adjust a relative angular orientation around the central longitudinal axis (Ai) between the left and right sets of treatment transducers (20iL, 20iR), in that each of the several modules comprises an adjusting mechanism (36i) for separately adjusting a distance between the left and right lateral sections of the support structure (34iL, 34iR), so as to adjust the distance between the left and right sets of treatment transducers (20iL, 20iR), in that the adjusting mechanism comprises a lock (40i) for maintaining, in use of the ultrasound generating treating device, a constant distance and a constant relative angular orientation around the central longitudinal axis between the left and right sets of treatment transducers (20iL, 20iR), and in that the left and right lateral sections (34iL, 34iR) have ultrasonic imaging transducers (42iL, 42iR) for forming respectively a left and a right image of an emission zone of the left and right sets of treatment transducers (20iL, 20iR) held on respective sections (34iL, 34iR), wherein at least two of the several modules (34i) of the support structure (32) are articulated (46) to allow a relative angular movement between the at least two of the several modules (34i) around an axis extending along the lateral direction.

6. The external device according to claim 5, characterized in that the at least two of the several modules (34i) of the support structure are articulated through a flexible module connector (46).

7. An apparatus for inducing spinal cord and/or spinal nerve treatment by emission of ultrasound waves, comprising:
the external ultrasound generating treating device (12) according to claim 5;
a generator (10) to supply electricity to the external ultrasound generating treating device; and
a controller (15).

8. A method for transiently opening the blood-spinal cord barrier and/or the blood spinal nerves barrier in at least one treatment zone of the spinal cord and/or spinal nerves of a patient, said method comprising:
positioning externally against the back of the patient an external ultrasound generating treating device (12) comprising an array of several ultrasound generating treatment transducers (20iL, 20iR) distributed along a longitudinal direction and a lateral direction, wherein the external ultrasound generating device comprises a support structure (32) having several modules (34i), each of the several modules comprising at least two sets of ultrasound generating treatment transducers, a left set (20iL) being located on a left lateral side of the back of the patient with respect to the spine of the patient and having a left emission zone, and a right set (20iR) being located on a right lateral side of the back of the patient with respect to a spine of the patient and having a right emission zone, wherein the support structure (32) maintains, in use of the external ultrasound generating treating device, a constant distance and a constant relative angular orientation around a central longitudinal axis (Ai) between the left and right sets of treatment transducers (20iL, 20iR), and wherein each of the several modules (34i) have an adjusting mechanism (36i) for adjusting, around the central longitudinal axis (Ai), a relative angular orientation between respective left and right sets of treatment transducers (20iL, 20iR), and for separately adjusting a distance between the left and right sets of treatment transducers (20iL, 20iR), wherein the adjusting mechanisms (36i) of each of the several modules (34i) are mechanically connected for simultaneous adjustment;
forming at least one left image along a left imaging axis having a set orientation with respect to the left emission zone and one right image along right imaging axis having a set orientation with respect to the right emission zone by generating ultrasound beams;
orienting the left and right emission zones according to the left and right images so that the left and right ultrasound emission zones are at least partially superposed on a treatment zone, wherein orienting the left and right emission comprises orienting the sets of treatment transducers (20iL, 20iR) according to the left and right images so that the left and right ultrasound emission zones are at least partially superposed on the treatment zone, and wherein the treatment zone extends throughout an extension of several vertebrae of the patient.

9. The method according to claim 8, comprising intravenously injecting an ultrasound contrast agent in a blood circulation system of the patient, prior to and/or during generation of the ultrasound treatment beams.

10. The method according to claim 8, wherein at least one of the ultrasound treatment beams has a resonant frequency ranging from 0.5 to 4 MHz.

11. The method according to claim 8, wherein a pressure level of at least one of the ultrasound treatment beams is calculated to obtain a pressure level within the spinal cord and/or spinal nerve tissues between 0.8 MPa and 3.0 MPa.

12. The method according to claim 8, wherein an application of the ultrasound treatment beams is determined to obtain a mechanical index (MI) within the spinal cord and/or spinal nerve tissues of from 0.3 to 3.0.

13. A method of treating at least one of:
- a spinal degenerative pathology;
- a spinal cord tumor disease; and
- a spinal inflammatory pathology using the method of claim 8.

14. The method of claim 13, wherein the spinal degenerative pathology is amyotrophic lateral sclerosis (ALS), the spinal cord tumor disease is spinal astrocytomas, and the spinal inflammatory pathology is multiple sclerosis.

15. A method of improving repair and/or rehabilitation of a spinal cord and/or spinal nerve(s), including using cell transplant and/or stem cell regeneration by treating the spinal cord and/or spinal nerves using the method of claim 8.

16. A method for transiently opening the blood-spinal cord barrier and/or the blood spinal nerves barrier in at least one treatment zone of the spinal cord and/or spinal nerves of a patient, said method comprising:

positioning externally against the back of the patient an external ultrasound generating treating device (12) comprising an array of several ultrasound generating treatment transducers (20*i*L, 20*i*R) distributed along a longitudinal direction and a lateral direction, wherein the external ultrasound generating device comprises a support structure (32) having several modules (34*i*), each of the several modules comprising at least two sets of ultrasound generating treatment transducers, a left set (20*i*L) being located on a left lateral side of the back of the patient with respect to the spine of the patient and having a left emission zone, and a right set (20*i*R) being located on a right lateral side of the back of the patient with respect to a spine of the patient and having a right emission zone, wherein the support structure (32) maintains, in use of the external ultrasound generating treating device, a constant distance and a constant relative angular orientation around a central longitudinal axis (Ai) between the left and right sets of treatment transducers (20*i*L, 20*i*R), and wherein each of the several modules (34*i*) have an adjusting mechanism (36*i*) for adjusting, around the central longitudinal axis (Ai), a relative angular orientation between respective left and right sets of treatment transducers (20*i*L, 20*i*R), and for separately adjusting a distance between the left and right sets of treatment transducers (20*i*L, 20*i*R), wherein at least two of the several modules (34*i*) of the support structure (32) are articulated (46) to allow a relative angular movement between the at least two of the several modules (34*i*) around an axis extending along the lateral direction;

forming at least one left image along a left imaging axis having a set orientation with respect to the left emission zone and one right image along right imaging axis having a set orientation with respect to the right emission zone by generating ultrasound beams;

orienting the left and right emission zones according to the left and right images so that the left and right ultrasound emission zones are at least partially superposed on a treatment zone, wherein orienting the left and right emission comprises orienting the sets of treatment transducers (20*i*L, 20*i*R) according to the left and right images so that the left and right ultrasound emission zones are at least partially superposed on the treatment zone, and wherein the treatment zone extends throughout an extension of several vertebrae of the patient.

17. A method of treating at least one of:
- a spinal degenerative pathology;
- a spinal cord tumor disease; and
- a spinal inflammatory pathology using the method of claim 16.

18. The method of claim 17, wherein the spinal degenerative pathology is amyotrophic lateral sclerosis (ALS), the spinal cord tumor disease is spinal astrocytomas, and the spinal inflammatory pathology is multiple sclerosis.

19. A method of improving repair and/or rehabilitation of a spinal cord and/or spinal nerve(s), including using cell transplant and/or stem cell regeneration by treating the spinal cord and/or spinal nerves using the method of claim 16.

* * * * *